United States Patent [19]

Keve et al.

[11] Patent Number: 4,680,397
[45] Date of Patent: Jul. 14, 1987

[54] APOVINCAMINOL DERIVATIVE

[75] Inventors: Tibor Keve; Béla Zsadon; György Fekete, all of Budapest; János Galambos, Érd; Margit Barta née Bukovecz, Budapest; László Szporny, Budapest; Lilla Forgács, Budapest; Árpád Király, Budapest; Gyöngyvér Soós, Budapest; Béla Kiss, Vecsés; Mária Zájer née Balázs, Budapest, all of Hungary

[73] Assignee: Richter Gedeon Vegyeszeti Gyar Rt., Budapest, Hungary

[21] Appl. No.: 727,130

[22] Filed: Apr. 25, 1985

[30] Foreign Application Priority Data

Apr. 25, 1984 [HU] Hungary ............... 1582/84

[51] Int. Cl.⁴ .................................... C07D 461/00
[52] U.S. Cl. ........................................ 546/51
[58] Field of Search ..................... 546/51; 514/267

[56] References Cited

U.S. PATENT DOCUMENTS

| | | | |
|---|---|---|---|
| 4,035,370 | 7/1977 | Lörincz et al. | 546/51 |
| 4,065,458 | 12/1977 | Lörincz et al. | 546/51 |
| 4,108,996 | 8/1978 | Lörincz et al. | 514/283 |
| 4,285,949 | 8/1981 | Hannart | 514/283 |
| 4,419,359 | 12/1983 | Keve et al. | 514/283 |
| 4,424,223 | 1/1984 | Keve et al. | 514/283 |
| 4,424,224 | 1/1984 | S antay et al. | 514/283 |
| 4,432,982 | 2/1984 | Szantay et al. | 514/283 |

FOREIGN PATENT DOCUMENTS

| | | | |
|---|---|---|---|
| 2094787 | 9/1982 | United Kingdom | 514/283 |
| 2158066 | 11/1985 | United Kingdom | 546/51 |

OTHER PUBLICATIONS

Caron-Sigaut, et al., Chemical Abstracts, vol. 92, 22665x (1980).
Olivier, et al., Chemical Abstracts, vol. 75, 88814a (1971).
Balazs, et al., Chemical Abstracts, vol. 94, 202488s (1981).
Zarjer, et al., Chemical Abstracts, vol. 95, 225670e (1981).

Primary Examiner—Donald G. Daus
Assistant Examiner—Diana G. Rivers
Attorney, Agent, or Firm—Keil & Weinkauf

[57] ABSTRACT

The invention relates to new apovincaminol derivatives of the formula /I/

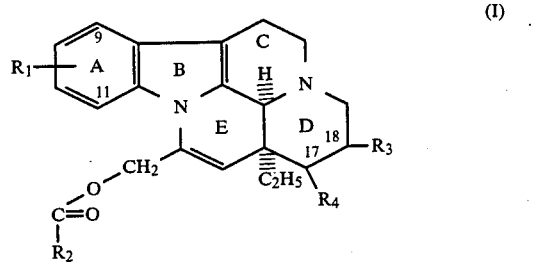

wherein
$R_1$ is hydrogen, nitro or halogen,
$R_2$ is a substituted or unsubstituted alkyl or phenyl group,
$R_3$ and $R_4$ together form a valency bond or each independently represents hydrogen, hydroxyl or an $-OR_5$ group, in which
$R_5$ is substituted or unsubstituted alkanoyl or benzoyl group, with the proviso that if $R_2$ stands for a 3,4,5-trimethoxyphenyl group and $R_1$ is hydrogen, $R_3$ and $R_4$ together do not form a valency bond, or if $R_2$ is a 3,4,5-trimethoxyphenyl group and $R_3$ and $R_4$ both are hydrogen, $R_1$ is other than hydrogen, nitro or bromine, and acid addition salts thereof.

The compounds may be used in the therapy of various skin diseases accompanied by a pathological cell proliferation, preferably psoriasis.

1 Claim, No Drawings

APOVINCAMINOL DERIVATIVE

The invention relates to new apovincaminol derivatives of the formula I

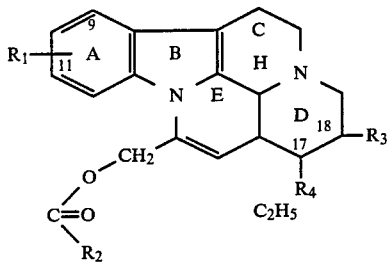

wherein
$R_1$ is hydrogen, nitro or halogen,
$R_2$ is a substituted or unsubstituted alkyl or phenyl group,
$R_3$ and $R_4$ together form a valency bond or each independently represents hydrogen, hydroxyl or an —$OR_5$ group, in which
$R_5$ is substituted or unsubstituted alkanoyl or benzoyl group,
with the proviso that if $R_2$ stands for a 3,4,5-trimethoxyphenyl group and $R_1$ is hydrogen, $R_3$ and $R_4$ together do not form a valency bond, or if $R_2$ is a 3,4,5-trimethoxyphenyl group and $R_3$ and $R_4$ both are hydrogen, $R_1$ is other than hydrogen, nitro or bromine, and acid addition salts thereof.

$R_1$ as halogen preferably stands for bromine or chlorine; $R_2$ as an alkyl group preferably represents a straight or branched chained alkyl group having from 1 to 20, preferably 1 to 15, more preferably 1 to 6 carbon atoms, e.g. methyl, ethyl or pentadecyl group. In the definition of $R_2$ phenyl is optionally substituted preferably by one or more nitro and/or methoxy groups. In the definition of $R_5$ the term "alkanoyl" is used to refer to straight or branched chained alkanoyl group, preferably having from 1 to 20, more preferably 1 to 15, most preferably 1 to 6 carbon atoms, e.g. acetyl; and the benzoyl group is preferably substituted by methoxy, thus preferably is a 3,4,5-trimethoxybenzoyl group.

The compounds of the formula I are new. Structurally related compounds are for example disclosed in the Belgian Patent Specification Nos. 892 069, 891 991 and 892 070, wherein apovincaminol and 17,18-dehydroapovincaminol trimethoxybenzoates, and the 9-nitro-, 11-nitro-, 10-bromo-, 11-bromo- and 10-methoxyapovincaminol trimethoxybenzoates are described. According to the literature these compounds effectively inhibit the phosphodiesterase enzyme activity and are particularly suitable for treating skin diseases accompanied by pathological cell proliferation.

The compounds according to the invention may also be used in the therapy of various skin diseases and in addition to their excellent activity, they are advantageous in that their photostability is considerably better than that of the hitherto known compounds. It is known that skin diseases accompanied by a pathological proliferation of epidermis are relatively frequent and include both benign and malignant diseases. Certain diseases are characteristic for human beings while others may be observed on animals as well.

Since a part of the skin diseases accompanied by a pathological cell proliferation does not occur on animals, e.g. psoriasis, the antipsoriatic activity of the compounds can only be demonstrated in animals tests indirectly.

Voorhees et al. (Arch. Derm. 104, 359–365 (1971)) established that the pathological proliferation is accompanied by the decrease of the level of cyclic adenozine monophosphate (c-AMP). As it is well known, c-AMP is produced by adenyl cyclase and is decomposed by phosphodiesterase. Voorhees successfully influenced psoriasis by agents stimulating the activity of adenyl cyclase (e.g. norephinephrine) or inhibiting the activity of phosphodiesterase (e.g. papaverine).

In our model experiments we verified that the compounds showing in vitro a phosphodiesterase inhibitory activity proved effective in clinical treatment of psoriasis.

The model experiments were performed by means of phosphodiesterase isolated from animal tissues (rat brain, cattle brain, cattle heart). The enzyme was isolated by the technique of J. Schroder and H. V. Richenberg (Biochem. Biphys. Acta 302, 50 (1973)) whereupon the phosphodiesterase isolated was purified according to the method of J. G. Hardman and E. W. Sutherland (J. Biol. Chem. 240, 3704 (1965)) and the activity of the purified enzyme was measured by a radioisotopic method developed by G. Poch, in an incubator, first without the inhibitory substance and then in the presence of the test substance as an inhibitory agent, after an incubation time of 20 minutes (N.S. Arch. Pharmacol. 268, 272 (1971)). From the test compounds a 1 mmole stock solution was prepared with aqueous hydrochloric acid solution and different amounts of the stock solution were added to the enzyme preparates corresponding to $5 \times 10^{-6}$, $1 \times 10^{-5}$ and $5 \times 10^{-5}$ mole/lit. of the test compound. A solution of papaverine used as reference compound is added to the enzyme preparate in an analogous manner.

The activity of the solutions of the test compound and papaverine was expressed in percents of the test compound and papaverine was expressed in percents of the control (enzyme solution without any inhibitory substance, 100%).

The tests on an enzyme isolated from cattle brain and cattle heart, respectively were carried out in an analogous way. On the basis of the results obtained the enzyme activity was plotted against the logarithm of the concentration of enzyme inhibitor ($\mu$moles) and from the curve inhibitor concentration, which resulted in a 50% decrease of enzyme activity was read off ($I_{50}$). The results obtained are shown in Table 1.

TABLE 1

| Code number Test compound | Substituent definitions in Formula(I) | | | | $I_{50}(\mu moles)$ | | |
|---|---|---|---|---|---|---|---|
| | $R_1$ | $R_2$ | $R_3$ | $R_4$ | rat brain | cattle brain | cattle heart |
| papaverin hydrochloride | — | | | | 120 | 100 | 50 |
| 886 (9-nitro-17,18-dehydro-apovincaminol acetate) | nitro | methyl | valency | bond | 50 | n.d. | n.d. |
| 887(11-nitro-17,18-dehydro- | nitro | methyl | valency | bond | 30 | n.d. | n.d. |

TABLE 1-continued

| Code number Test compound | Substituent definitions in Formula(I) | | | | rat brain | 150(μmoles) cattle brain | cattle heart |
|---|---|---|---|---|---|---|---|
| | $R_1$ | $R_2$ | $R_3$ | $R_4$ | | | |
| apovincaminol acetate) | | | | | | | |
| 888(9-nitro-17,18-dehydro-apovincaminol 3',4',5'-trimethoxybenzoate | nitro | 3,4,5-trimethoxy-phenyl | valency bond | | 30 | 10 | 5 |
| 889(11-nitro-17,18-dehydro-apovincaminol 3',4',5'-tri-methoxybenzoate | nitro | 3,4,5-trimethoxy-phenyl | valency bond | | 10 | 5 | 2 |
| 956/18β-O—acetyl-apovinca-minol O—acetate) | H | methyl | —O—acetyl | H | 30 | 30 | 25 |
| 1041(18β-hydroxyapovinca-minol acetate | H | methyl | hydroxyl | H | 120 | 100 | 60 |
| 1079(18β-hydroxyapovin-caminol 3',4',5'-trimethoxy-benzoate) | H | 3,4,5-trimethoxy-phenyl | hydroxyl | H | 5 | 5 | 2 | n.d. = no data

The results set forth in the table clearly show that the new compounds according to the invention on an enzyme isolated from cattle brain, cattle heart and rat brain, respectively were multifold more effective than papaverine used as reference substance.

The first clinical tests were carried out with preparations for topical use (e.g. ointments, creams, solutions, tinctures, pastes, aerosols, etc.) containing the new compounds according to the invention as an active ingredient. More particularly, creams containing 2%, 1%, 0.5%, 0.25% and 0.11%, resp. of active ingredient were employed.

Clinical tests were performed on patients suffering from psoriasis. During the tests the patients have not received any systemic, e.g. immunsupressive, citostatic or glucocorticoid treatment for their basic disease.

Groups of 5 were examined by the so-called plaque method. One side of symmetrical skin lesions was treated by a cream containing the active ingredient in the desired concentration, while on the other side placebo was applied. The remaining psoriatic sites on the skin were subjected to other topical treatments for example with ointments containing flumethasone pivalate and salicylic acid, as active ingredient, which are widely used for the treatment of psoriasis.

The test were started with creams having a higher active ingredient concentration and then further patients were treated with preparations containing the smallest active ingredient concentration. The skin was treated 2 to 3 times a day until the symptoms disappeared or were considerably improved (1 to 6 weeks).

The efficiency was evaluated upon observing three symptoms: inflammation, infiltration and desquamation (peeling). The intensity of the symptoms was qualified by scores between 0 and 3. The results were evaluated by methods of mathematical statistics.

The results unambiguously prove that the compositions can successfully be used for treating psoriasis. No side effects were observed in any of the tests.

According to an aspect of the invention there is provided a process for preparing new apovincaminol derivatives of the formula (I)

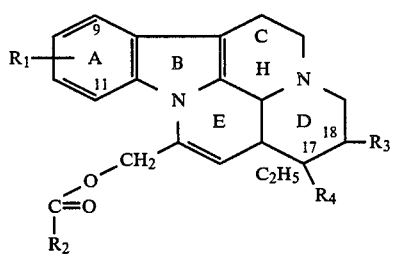

(I)

wherein the substituents are as hereinbefore defined, and acid addition salts thereof by (a) reacting an apovincaminol derivative of the formula II

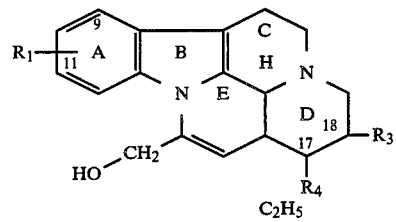

II wherein the substituents are as defined in connection with formula I, with an acid of the formula III $R_2$—COOH    III or a reactive derivative thereof wherein $R_2$ is as defined hereinabove, or (b) nitrating and/or halogenating and/or hydroxylating and/or acylating a compound of the formula I, wherein $R_2$ is as defined above, $R_1$ *is hydrogen*, $R_3$ and $R_4$ together form a valency bond, and if desired, converting a compound of the formula I obtained into an acid addition salt thereof.

According to another aspect of the invention there are provided pharmaceutical compositions having a phosphodiesterase inhibiting activity, in particular for treating and prophylaxis of skin diseases accompanied by a pathological cell proliferation which comprise as active ingredient a pharmaceutically effective amount of a compound of the formula I or a pharmaceutically acceptable acid addition salt thereof in association with at least one pharmaceutically inert carrier or diluent and optionally further pharmaceutically active substances.

Compounds of the formula II used as starting materials in the process according to the invention are partially new, partially known in the art. Compounds of formula II, in which $R_1$ is hydrogen or nitro or bromine, $R_3$ and $R_4$ represent a double bond are known and are disclosed in the Belgian Patent Specification Nos. 891 991, 892 069 and 892 070. The preparation of the new compounds of the formula II is exhaustively exemplified in the present specification. The compounds of the formula (III) are known in the art. Suitable derivatives include the acid halides.

The acylation according to the invention is carried out in the presence of an organic solvent, preferably benzene or a homologue thereof, chlorinated hydrocarbons or aliphatic ketons or pyridine.

If the reaction is carried out with a suitable derivative of the acid of the formula III, e.g. with a 3,4,5-trimethoxy-benzoyl halide, an acid binding agent is added to the reaction mixture in an amount equivalent to the halogenic acid formed in the reaction or in a slight excess. As an acid binding agent for example alkali metal carbonates, alkali metal hydrocarbonates or organic basic amides, such as pyridine can be employed. If the reaction is carried out with the acid of the formula III, preferably 3,4,5-trimethoxy-benzoic acid, a catalytic amount of an acid, preferably hydrochloric acid or sulfuric acid or a carboxyl activator and/or a dehydrating agent is added to the reaction mixture. As a carboxyl activator for example halogenated phenols, preferably pentachlorophenol, as a dehydrating agent for example N,N'-dicyclohexyl-carbodiimide may be employed. The acylation is carried out at a temperature between $-20°$ C. and the boiling temperature of the reaction mixture, preferably 20° C. and 60° C.

The product is isolated from the reaction mixture generally by extraction and/or evaporation.

Alternatively, according to process b the nitration and/or halogenation in the A- and B-ring and the acylation in the D-ring may be carried out after the hydroxilation and/or introduction of the $R_2$ group.

If desired, the product obtained may be converted into an acid addition salt thereof. Preferred representatives of the inorganic acid addition salts are e.g. chlorohydrate, sulfate and phosphate salts. The preferred organic acid addition salts include the hydrogentartarate, succinate, citrate and ascorbate salts. The salts are for example prepared by adding an alcoholic, ethereal or acetone solution of the acid component to the product of formula I. The preparation of salts is preferably performed between pH 3 and pH 6.

The pharmaceutical compositions according to the invention contain 0.1 to 8.0% by weight, preferably 0.2 to 2.0% by weight of active ingredient. The compositions optionally contain also further pharmaceutically active ingredients, e.g. antibiotics, citostatic agents, prostaglandins, ditranol, salicylic acid, tar, anti-inflammatory agents, immunosupressive agents, glucocorticoids and in case of parenteral administration local anaesthetics. As a glucocorticoid preferably triamcinolon acetonide is employed. The compositions preferably are finished as formulations suitable for topical, local application, e.g. creams, ointments, solutions, gelées, aerosols, aerosol foams, plasters, etc.

The active ingredient preferably is incorporated into a cream, easy to wash down.

Creams are prepared by dissolving the active ingredient in an alcoholic solvent, preferably propylene or dipropylene glycol or a mixture thereof with water and subsequently admixing the solution obtained with a well smearable, skin compatible fatty phase.

The fatty phase may contain cetyl, stearyl, cetostearyl alcohol, paraffine oil, glycerine monostearate, etc.

The creams may further contain emulsifying agents, preferably polyoxyethylene-sorbitane monooleate or monostearate and preserving agents, e.g. various benzoic acid derivatives, preferably p-hydroxy-benzoic acid methyl ester.

The creams preferably contain 0.25 to 2.0% by weight of active ingredient, 45 to 50% by weight of glycol, 23 to 27% by weight of paraffine oil, 11 to 15% by weight of stearyl alcohol and further additive(s) up to 100%.

The active ingredient may be formulated also as an ointment which cannot be washed down with water. In this case the active ingredient is directly incorporated into the fatty phase.

Solutions may be prepared for example with 20 to 40% by weight of propylene glycol or dipropylene glycol, 40 to 55% by weight of a 96% ethanol and distilled water up to 100%.

Aerosol formulations are prepared by adding a solution of the active ingredient in propylene glycol, a fat, preferably isopropyl myristate and a suitable propellant, preferably freon.

An aerosol foam may for example be prepared by adding an alcoholic solution of the active ingredient to a mixture of 0.5 to 1.5% by weight of cetostearyl alcohol, 1 to 3% by weight of benzyl alcohol, 15 to 20% by weight of polyoxyethylene-sorbitane monooleate or monostearate and 25 to 30% by weight of water followed by the addition of freon.

For parenteral administration preferably injection solutions suitable for subcutaneous or intracutaneous administration are prepared. For this purpose a salt of the active ingredient is dissolved in a 0.72% aqueous sodium chloride solution and the pH of the solution is adjusted to 5.

The invention is further illustrated by the following examples which are not intended to limit the scope of the invention in any way.

EXAMPLE 1

9-Nitro-17,18-dehydroapovincaminol acetate (A) 9-Nitro-17,18-dehydroapovincamine 15 g (45 mmoles) of 17,18-dehydroapovincamine (prepared as described in the Belgian Patent Specification No. 892 069) and U.S. Pat. No. 4,424,223 are dissolved in a mixture of 75 ml of glacial acetic acid and 75 ml of dry acetonitrile and the solution is cooled to $-5°$ C. As a nitrating agent 60 ml of fuming nitric acid are admixed with 30 ml of glacial acetic acid and 30 ml of dry acetonitrile, the mixture is cooled to $-5°$ C. while the nitrous gases are expelled by bubbling nitrogen gas through the mixture.

The nitrating mixture is added to the solution of dehydroapovincamine dropwise, under vigorous stirring and cooling with ice/salt in 10 minutes, taking care that the temperature should remain between $-5°$ C. and 0° C. Stirring and cooling are then continued for 15 minutes, whereupon the reaction mixture is poured onto 600 g of ice and neutralized by careful addition of solid sodium carbonate. The precipitated bases are extracted with chloroform, the chloroform solution is extracted by shaking with water, dried over sodium sulfate and evaporated to dryness. As a residue 17.5 g of a crude base mixture are obtained.

As an evaporation residue of the first eluate fraction 5.4 g (14.2 mmoles; 31.7%) of 9-nitro-17,18-dehydroapovincamine are obtained, which are then recrystallized from ethanol.

Formula: $C_{21}H_{21}O_4N_3$ (molar mass: 379).
Melting point: 140° to 142° C.
$[\alpha]_D^{20} = +456°$ (chloroform).
U.V. spectrum (methanol) $\lambda_{max}$: 217, 247 and 293 nm.

Evaporation of the following eluate fraction yields 4.8 g (12.7 mmoles; 28%) of 11-nitro-17,18-dehydroapovincamine, which is then crystallized from alcohol.

Formula: $C_{21}H_{21}O_4N_3$ (molar mass: 379).
Melting point: 153° to 154° C.
$[\alpha]_D^{20} = +81°$ (chloroform).
U.V. spectrum (methanol) $\lambda_{max}$: 218, 258 and 333 nm.

(B) 9-Nitro-17,18-dehydroapovincaminol 1.5 g (4 mmoles) of 9-nitro-17,18-dehydroapovincamine are dissolved in 50 ml of absolute ethanol, 1.5 g of lithium borohydride are added to the solution, and the mixture is allowed to stand at room temperature overnight. The solution is diluted with 250 ml of water, whereupon the precipitated bases are extracted with three 50-ml portions of benzene. The combined benzene solutions are reextracted with water, dried over sodium sulfate and evaporated. As a residue 1.32 g of a crude product are obtained, which is then chromotographed on an alumina column having Brockmann-II activity. By elution with a 98: 2 (vol./vol.) mixture of benzene and absolute ethanol the fraction containing pure 9-nitro-17,18-dehydroapovincaminol is separated, and evaporated to yield 1.05 g (3 mmoles, 75%) of an amorphous product.

Formula: $C_{20}H_{21}O_3N_3$ (molar mass: 351).
$[\alpha]_D^{20} = -127°$ (methanol).
U.V. spectrum (methanol) $\lambda_{max}$: 217, 279 and 288 nm.

(C) 9-Nitro-17,18-dehydroapovincaminol acetate 0.9 g (2.8 mmoles) of 9-nitro-17,18-dehydroapovincaminol are dissolved in 60 ml of absolute chloroform, 5 ml of absolute pyridine and 2.4 g of acetyl chloride are added and the mixture is allowed to stand overnight. It is then poured onto 200 ml of ice water and alkalized under cooling. The phases are separated and the alkaline aqueous phase is extracted with two further 40-ml portions of chloroform. The combined chloroform phases are reextracted by shaking with 50 ml of water, dried over sodium sulfate and evaporated to dryness. As a residue 1.04 g (2.65 mmoles, 94%) of 9-nitro-17,18-dehydroapovincaminol acetate are obtained. The product is crystallized from ethanol.

Formula: $C_{22}H_{23}O_4N_3$ (molar mass: 393).
$[\alpha]_D^{20} = +88°$ (chloroform).
U.V. spectrum (methanol): $\lambda_{max}$: 217, 280 and 287 nm.
Melting point: 164° 1 to 166° C.

EXAMPLE 2

9-Nitro-17,18-dehydroapovincaminol 3',4',5'-trimethoxybenzoate 1.05 g (3 mmoles) of 9-nitro-17,18-dehydroapovincaminol are dissolved in 40 ml of absolute benzene, 1 ml of absolute pyridine and 1.0 g of 3,4,5-trimethoxybenzoyl chloride are added (4.3 mmoles) and the mixture is allowed to stand at 40° C. for two hours. The reaction mixture is diluted with benzene to twice of its original volume, and shaken with 20 ml of a 1 n sodium hydroxide solution precooled with ice. The aqueous phase is shaken with 40 ml of benzene, the combined benzene solutions are reextracted with 30 ml of water and the product is dried and chromatographed on a column filled with 20 g of alumina. Evaporation of the eluate containing the pruified product yields 0.75 g (1.38 mmoles, 46%) of 9-nitro-17,18-dehydroapovincaminol trimethoxybenzoate;

Formula: $C_{30}H_{31}O_7N_3$ (molecular mass: 545).
$[\alpha]_D^{20} = +38°$ (chloroform).
U.V. spectrum (methanol) $\lambda_{max}$: 215 and 284 nm.

EXAMPLE 3

11-Nitro-apovincaminol acetate 1.05 g (3 mmoles) of 11-nitro-apovincaminol (prepared according to the Belgian Patent Specification No. 891,991 and Example 1 of U.S. Pat. No. 4,419,359) are acetylated as described in Example 2 to yield 1.1 g (2.8 mmoles) of 11-nitro-apovincaminol acetate, which are then crystallized from ethanol.

Formula: $C_{22}H_{23}O_4N_3$ (molecular mass: 393).
$[\alpha]_D^{20} = -150°$ (chloroform).
Melting point: 155° to 156° C.
U.V. spectrum (methanol) $\lambda_{max}$: 208, 248 and 259 nm.

EXAMPLE 4

18β-O-acetoxy-apovincaminol acetate (A) 18β-Hydroxy-apovincamine 11.1 g (30 mmoles) of 18β-hydroxy-vincamine are dissolved in 200 ml of absolute chloroform, formic acid is added to the solution, which is then dehydrated with acetyl chloride. Evaporation of the reaction mixture yields 11 g of a crude product chiefly containing the desired dihydroxy-compound and, in a smaller amount, the acetylated derivative thereof. The mixture is dissolved in 150 ml of absolute ethanol containing 2 g of freshly prepared sodium ethylate and desacetylated by allowing to stand at room temperature for 1.5 hours. The desacetylated mixture is evaporated to 20 ml, poured onto 200 ml of ice water and extracted with five 50-ml portions of benzene. The combined benzene phases are shaken with 50 ml of water, dried over sodium sulfate and decoloured by passing through a column filled with 50 g of alumina. The adsorbent is washed through with benzene. Evaporation of the decoloured benzene solution affords 9.37 g of pure 18β-hydroxy-apovincamine (26.6 mmoles, 88.6%) as an amorphous product.

Formula: $C_{21}H_{24}O_3N_2$ (molar mass: 352).
$[\alpha]_D^{20}$: +134° (chloroform).

From a 1 n solution of the base its hydrochloride is prepared in the usual manner.

Formula: $C_{21}H_{24}O_3N_2 \cdot HCl$.
Melting point: 120° to 122° C.
$[\alpha]_D^{20} = +100°$ (ethanol).
U.V. spectrum (methanol) $\lambda_{max}$: 204, 229, 274 and 314 nm.

(B) 18β-Hydroxy-apovincaminol and hydrochloride thereof 7.0 g (20 mmoles) of 18β-hydroxy-apovincamine are reduced with lithium aluminium hydride in an absolute ethereal solution as described in Example 1. As evaporation residue 6.15 g (19 mmoles, 95%) of 18β-hydroxyapovincaminol base are obtained.

Melting point (after recrystallization from benzene): 105° C. (decomp.).

Formula: $C_{20}H_{24}O_2N_2$ (molar mass: 324).

The product is then converted to its hydrochloride with 1 n hydrochloric acid.

Formula: $C_{20}H_{24}O_2N_2.HCl$.

Melting point: 190° to 192° C. (decomp.).

U.V. spectrum (methanol) $\lambda_{max}$: 224, 256, 301 and 312

(C) 18β-Acetoxy-apovincaminol acetate 1.62 g (5 mmoles) of 18β-hydroxy-apovincaminol are dissolved in 50 ml of absolute chloroform, 2 ml of pyridine and 1.6 g (20 mmoles) of acetyl chloride are added, and the mixture is allowed to stand at room temperature overnight. The solution is then poured onto 200 ml of ice water, the aqueous phase is alkalized and the two phases are shaken several times. The aqueous phase is separated and shaken with two 30-ml portions of chloroform, the combined chloroform phases are reextracted by shaking with 20 ml of water, dried over sodium sulfate and evaporated to dryness. As an evaporation residue 1.75 g of amorphous product are obtained, which are dissolved in benzene and decoloured by passing through a column filled with 10 g of alumina. Evaporation of the benzene eluate yields 1.6 g (3.92 mmoles, 78%) of pure 18β-acetoxy-apovincaminol acetate, which is then crystallized from alcohol.

Formula $C_{24}H_{28}O_4N_2$ (molar mass: 408).

Melting point: 122° to 124° C.

$[\alpha]_D^{20} = +18°$ (chloroform).

U.V. spectrum (methanol) $\lambda_{max}$: 223, 251, 301 and 311 nm.

EXAMPLE 5

(A) 18β-Acetoxy-apovincaminol acetate 1.62 g (5 mmoles) of 18β-hydroxy-apovincaminol are acylated with 1.2 g (15 mmoles) of acetyl chloride following the procedure described in Example 4C). The product is chromatographed on a column filled with 100 g of alumina (Brockmann-II activity), using benzene for the elution. As a benzene eluate 0.84 g (2.06 mmoles; 41%) of 18β-acetoxy-apovincaminol acetate are obtained.

Elution is then continued with a 98:2 (vol./vol.) mixture of benzene and ethanol. Evaporation of the first eluate fraction obtained yields 0.28 g (0.77 mmoles; 15%) of 18β-acetoxy-apovincaminol, the structure of which could be verified also by mass spectrometry.

Formula: $C_{22}H_{26}O_3N_2$ (molar mass: 266).

Melting point (after crystallization from ethanol): 119° to 120° C.

$[\alpha]_D^{20} = 0°$ (ethanol).

Acetyl content: 12%.

U.V. spectrum (methanol) $\lambda_{max}$: 225, 257, 302 and 313 nm.

(B) 18β-Hydroxy-apovincaminol acetate 1.62 g (5 mmoles) of 18β-hydroxy-apovincaminol are acylated with 0.66 g (8.4 mmoles) of acetyl chloride following the procedure described in Example 4C). The product mixture is chromatographed on a column filled with 100 g of alumina having Brockmann-II activity.

After elution with benzene 0.5 g (1.23 mmoles; 24.5%) of 18β-acetoxy-apovincaminol acetate are isolated.

Elution is continued with a 98:2 (vol./vol.) mixture of benzene and ethanol. By evaporation of the first eluate fraction obtained with this mixture 0.17 g (0.46 mmoles, 9.3%) of 18β-acetoxy-apovincaminol are obtained.

Evaporation of the next eluate fraction yields 0.85 g (2.32 mmoles, 46.5%) of 18β-hydroxy-apovincaminol-14-acetate.

Formula: $C_{22}H_{26}O_3N_2$ (molar mass: 366L).

$[\alpha]_D^{20} = -20°$ (ethanol).

acetyl content: 11.9%.

U.V. spectrum (methanol) $\lambda_{max}$: 225, 257, 302 and 313 nm.

EXAMPLE 6

18β-Hydroxy-apovincaminol 3′,4′,5′-trimethoxybenzoate 2.27 g (7 mmoles) of 18β-hydroxy-apovincaminol are acylated with 1.10 g (14 mmoles) of 3,4,5-trimethoxybenzoyl chloride, following the procedure described in Example 4.

The product mixture is fractionated on a chromatographic column filled with 100 g of alumina. After elution with benzene and subsequently with a 98:2 (vol./vol.) mixture of benzene and ethanol 1.05 g (2.03 mmoles, 29%) of 18β-hydroxy-apovincaminol trimethoxybenzoate, followed by 1.34 g (4.14 mmoles, 59%) of unchanged starting material are eluted.

18β-hydroxy-apovincaminol trimethoxybenzoate is an amorphous product.

Formula: $C_{30}H_{34}O_6N_2$ (molar mass: 518).

$[\alpha]_D^{20} = 0°$ (methanol, c=0.5).

U.V. spectrum (methanol) $\lambda_{max}$: 215, 258, 301 and 312 nm.

EXAMPLE 7

17,18-Dehydroapovincaminol p-nitro-benzoate 5.0 g 17,18-dehydroapovincaminol (16.3 mmoles) prepared according to the Belgian Patent Specification No. 892 069 are dissolved in 30 ml of absolute pyridine. There are added 4.5 g (24 mmoles) of p-nitro-benzoyl chloride, and the mixture is allowed to stand at room temperature for three hours. The greater part of pyridine is distilled off under reduced pressure, the residue is combined with 200 ml of ice water, alkalized with sodium hydroxide solution and extracted with three 50-ml portions of chloroform. The chloroform phase is shaken with water, dried over sodium sulfate and evaporated. The residue is dissolved in benzene and decoloured by passing through a column filled with 200 g of alumina, using benzene for the elution. 5.1 g of p-nitrobenzoate are obtained by evaporation of the eluate (11.2 mmoles, 69%). The product is crystallized from a mixture of 10 ml of benzene and 50 ml of ethanol to yield 4.4 g of crystalline 17,18-dehydroapovincaminol p-nitro-benzoate.

Formula: $C_{27}H_{25}O_4N_3$ (molar mass: 455).

Melting point: 175° to 176° C.

$[\alpha]_D^{20} = 0°$ (chloroform).

U.V. spectrum (methanol) $\lambda_{max}$: 227, 260, 303 and 314 nm.

EXAMPLE 8

18β-O-Palmitoyl-apovincaminol palmitate 0.66 of 18β-hydroxy-apovincaminol (2.03 mmoles) prepared as described in Example 4 A) are dissolved in 40 ml of cholroform, 2.8 ml of absolute pyridine and 2.8 g of palmitic acid chloride are added, and the mixture is allowed to stand at room temperature for two days. The solution is then shaken with 20 ml of a 2 n aqueous sodium hydroxide solution and subsequently two 20-ml portions of water, dried and evaporated to dryness. The evaporation residue is decoloured with 50 g of alumina in a benzene solution. Evaporation of the decoloured solution yields 4.58 g (1.98 mmoles, 97%) of palmitate, which is then recrystallized from 10 ml of acetone to yield 1.28 g of purified 18-O-palmitoyl-apovincaminol palmitate.

Formula: $C_{52}H_{84}O_4N_2$ (molar mass: 800).
Melting point: 56° to 58° C.
$[\alpha]_D^{20} = 0°$ (chloroform).
U.V. spectrum (methanol) $\lambda_{max}$: 224, 258, 301 and 312 nm.

EXAMPLE 9

18β-O-Benzoyl-apovincaminol benzoate

Following the procedure described in Example 8 but using benzoic acid chloride instead of palmitic acid chloride, the aimed compound is obtained.

Formula: $C_{34}H_{33}O_4N_2$ (molar mass: 533).
$[\alpha]_D^{20} = +59°$ (chloroform).
U.V. spectrum (methanol) $\lambda_{max}$: 224, 257, 301, 312 nm.

EXAMPLE 10

| | |
|---|---|
| 18β-acetoxy-apovincaminol acetate | 2 g |
| propylene glycol | 50 g |
| paraffine oil | 26 g |
| polyethylene glycol 400 | 5 g |
| stearyl alcohol | 15 g |
| glycerine monostearate | 2 g |

The active ingredient is dissolved in propylene glycol on water bath the temperature of which does not exceed 50° C. The other components are melted and then cooled to 40° to 45° C. under continuous stirring. Thereafter the solution of the active ingredient is added to the melt under stirring and the cream obtained is stirred until cooling down to room temperature.

EXAMPLE 11

| | |
|---|---|
| 11-nitro-apovincaminol acetate | 1.0 g |
| triamcinolone acetonide | 0.1 g |
| glycerine monostearate | 3.0 g |
| polyethylene glycol 400 | 5.0 g |
| stearyl alcohol | 13.0 g |
| paraffine oil | 24.9 g |
| propylene glycol | 53.0 g |

The procedure described in Example 10 is followed, except that two active ingredients are dissolved in propylene glycol.

EXAMPLE 12

| | |
|---|---|
| 9-nitro-17,18-dehydroapovincaminol 3',4', 5'-trimethoxybenzoate | 1% |
| propylene glycol | 30% |
| 96% ethanol | 69% |

From the above ingredients a tincture solution is prepared.

We claim:
1. 18β-Hydroxy-apovincaminol 3',4',5'-trimethoxybenzoate.

* * * * *